(12) United States Patent
Schmidt

(10) Patent No.: US 6,213,932 B1
(45) Date of Patent: Apr. 10, 2001

(54) INTERSTITIAL BRACHYTHERAPY DEVICE AND METHOD

(76) Inventor: Bruno Schmidt, 1322 Live Oak Pkwy., Tarpon Springs, FL (US) 34689

( * ) Notice: Subject to any disclaimer, the term of this patent is extended or adjusted under 35 U.S.C. 154(b) by 0 days.

(21) Appl. No.: 08/989,727

(22) Filed: Dec. 12, 1997

(51) Int. Cl.[7] ............................. A61N 5/00; A61M 31/00

(52) U.S. Cl. ............................................................ 600/7

(58) Field of Search ........................... 600/1–8; 604/57, 604/59, 60, 61, 62, 63, 64, 93; 221/22, 23, 67, 155; 227/176.1, 177.1

(56) References Cited

U.S. PATENT DOCUMENTS

| | | | |
|---|---|---|---|
| 2,620,796 | * 12/1952 | Eriksen et al. | 604/62 |
| 4,451,254 | * 5/1984 | Dinius et al. | 602/62 |
| 5,522,797 | * 6/1996 | Grimm | 604/61 |
| 5,860,909 | * 1/1999 | Mick et al. | 600/7 |

OTHER PUBLICATIONS

Author: Mick Radio–Nuclear Instruments, Inc. brochure entitled "Mick 200–TP applicator package".

* cited by examiner

Primary Examiner—Eric F. Winakur
(74) Attorney, Agent, or Firm—Stanley M. Miller

(57) ABSTRACT

A disposable, plastic interstitial brachytherapy device includes an applicator, having the general appearance of a hypodermic syringe, and a transparent plastic cartridge, detachably connected to the applicator, for holding a plurality of radioactive tumor-killing seeds. The seeds in the cartridge are urged toward a seed discharge chamber by a loop-shaped bias member that forms an integral part of the cartridge. The seed discharge chamber is a bore formed in the radially innermost end of the cartridge. That bore is aligned with an elongate throughbore formed in the applicator when the cartridge is inserted into a radially extending opening formed in the applicator. A manually-operated elongate plunger rod is slidably mounted in the elongate throughbore and drives seeds from the seed discharge chamber, through the needle, and into the tumor. The device is usable with conventional luer lock needles.

14 Claims, 2 Drawing Sheets

INTERSTITIAL BRACHYTHERAPY DEVICE AND METHOD

BACKGROUND OF THE INVENTION

1. Field of the Invention

This invention relates, generally, to surgical tools. More particularly, it relates to an apparatus that implants radioactive seeds into a prostate gland or other internal organ.

2. Description of the Prior Art

Surgical removal of the prostate, known as radical prostatectomy, became the treatment of choice for prostate cancer in the 1960s. The possible side effects of this procedure include loss of bladder control and impotence.

The percentage of patients who experience loss of impotency has been reduced in recent years by a new technique known as "nerve sparing radical prostatectomy." As its name implies, this procedure also includes the surgical removal of the prostate.

A nonsurgical mode of treatment, external beam radiation, has been used since the 1950s. This procedure produces lower rates of incontinence and impotency, but sometimes causes rectal problems since the rectum is radiated by the beam as well.

Still lower rates of incontinency and impotence result from the latest therapy, known as interstitial brachytherapy or radioactive seed implanting. In this technique, a predetermined number of radioactive pellets, known as seeds, that are about the size of a grain of rice, are implanted into a patient's prostate. In this way, radiation of the rectum and other organs near the prostate is minimized and such minimization, of course, reduces the risks of side effects.

There are two known methods for implanting the seeds. In the first method, a preloaded needle is used. A conventional luer lock eight inch needle is hand-loaded with seeds and spacers in the operating room. Seeds, and the spacers between them, can be easily dropped and any dropped seed must be found before the needle-loading procedure may continue; this is a rule mandated by the Nuclear Regulatory Commission, a federal agency charged with ensuring safe handling of radioactive devices, among other duties. After the needle is properly positioned in the prostate in accordance with a well-known procedure that need not be repeated here, a stylet, having a diameter smaller than that of the needle, is inserted into the needle behind the seeds and the spacers. The needle is then withdrawn over the stylet which remains in place; in this way, the seeds and spacers are constrained to remain in the prostate as the needle is withdrawn. The stylet is then withdrawn and the seeds and spacers remain in the prostate, the former to emit tumor-killing radiation and the latter as inert matter that does not interact with surrounding tissue.

An improved version of this procedure includes a plurality of seeds that are strung together by suture material, something like linked sausages. Thus, a string of seeds is inserted into the needle, thereby eliminating individual seed and spacer loading, greatly reducing the time it takes to load a needle, and essentially eliminating the problem with dropped seeds. The linked seeds are delivered in the same way, i.e., a stylet is placed behind the string in the needle and the needle is withdrawn from the prostate over the stationary stylet. The suture material eventually dissolves. The primary drawback of this procedure is that it requires continual reintroduction of seed strings as the procedure is performed. The number of seeds varies from patient to patient, but is usually between 40–100, with 70 being an average. Thus, in most cases, multiple strings are needed.

A device that includes a plurality of individual seeds in a artridge, known as the Mick (trademark) applicator system, after its inventor, is now in widespread use. The cartridge holds a large number of individual seeds which are loaded thereinto at a remote facility. the seeds can also be loaded into the cartridge at the hospital or at a nuclear pharmacy. This eliminates the time and cost of loading individual seeds in an operating room, eliminates the cost of manufacturing strings of suture-connected seeds, and eliminates the need to reload a needle with seed strings.

A seed-containing cartridge is attached to an applicator, in substantially the same way a magazine is attached to a weapon; the cartridge is spring-loaded to urge one seed at a time into a seed discharge chamber that holds a single seed at a time. A special hollow needle is connected to the leading end of the applicator. A plunger rod is inserted into a trailing end of the applicator and pushed forwardly, i.e., in a trailing-to-leading direction. The leading end of the plunger rod engages a seed in the seed discharge chamber and drives the seed into the hollow interior of the special needle and then out of the leading end of the needle into the prostate. The surgeon then withdraws the needle a predetermined distance, withdraws the plunger rod to a location on the trailing side of the seed discharge chamber so that another seed can enter the chamber from the cartridge, and that seed is then introduced into the prostate in the same way.

The grid system employed by physicians to ensure that the seeds are well-distributed throughout the prostate need not be described here because it is well-documented in the medical literature and forms no part of the invention described hereinafter.

The Mick applicator system decreases the amount of time required to implant a large plurality of seeds in a prostate and eliminates the risk of dropping individual seeds in an operating room. However, the system costs about $5,000.00, in part because the applicator is made of stainless steel, in part because the cartridge is machined and also made of stainless steel, and in part because the Mick system uses special needles that are reusable but which become dull as a result of such reuse.

The stainless steel components of the Mick applicator system are reusable because they can be disassembled, cleaned and then autoclaved. However, since the cartridge is not transparent, the number of seeds left therein cannot be easily ascertained unless the beginning number of seeds is known and the seeds are counted as they are implanted.

Thus, there is a need for an improved applicator system that is less expensive than the Mick applicator system, and which enables a surgeon to visually ascertain the number of seeds within a cartridge.

The Mick applicator system also has a utilitarian appearance that can be intimidating until a surgeon acquires familiarity with it. Thus, there is also a need for an interstitial brachytherapy applicator system having a physician-friendlier appearance.

Due to the expense of the Mick applicator system, it must be disassembled, cleaned, autoclaved and reused. Cleaning the nooks and crannies within the instrument is very difficult and time consuming. Autoclaving is also time-consuming and requires surgical procedures to be scheduled at long intervals. Built up blood and organic material can cause the spring loaded ball seat to freeze open, allowing a cartridge to fall out of the applicator if inverted. Thus, there is a need for a disposable interstitial brachytherapy device so that no time need be lost between patients.

However, in view of the art considered as a whole at the time the present invention was made, it was not obvious to those of ordinary skill in this art how an improved applicator system could be provided.

SUMMARY OF THE INVENTION

The longstanding but heretofore unfulfilled need for an apparatus that overcomes the limitations of the prior art is now met by a new, useful, and nonobvious invention. The novel interstitial brachytherapy device includes an applicator and a cartridge that is releasable connected to the applicator. The cartridge is adapted to hold a plurality of radioactive seeds there within in vertically stacked relation to one another.

The applicator includes an elongate barrel having an elongate throughbore formed therein coincident with a longitudinal axis of symmetry thereof.

A radially extending opening is formed in the barrel; the opening has a radially innermost end in open communication with the elongate throughbore. A seed discharge chamber is formed in the radially innermost end of the cartridge, and the seed discharge chamber aligns with the elongate throughbore when the cartridge is fully seated within the barrel. A manually-operated, elongate plunger rod is slidably mounted in the elongate throughbore, and an industry standard luer lock hollow needle is detachably secured to the barrel at a leading end thereof.

A bias means, integrally formed with the cartridge, urges the seeds in the cartridge toward the seed discharge chamber, said seed discharge chamber being sized to receive only one seed at a time. The bias means is preferably provided in the form of an inherently biased plastic spring.

The bias means has a leading end that is slidably received within the seed discharge chamber when the cartridge is empty.

Accordingly, retraction of the plunger rod to a preselected location on a trailing side of the seed discharge chamber enables the bias means to urge a seed into the seed discharge chamber when at least one seed is stored within the cartridge. Moreover, advancement of the plunger rod from the preselected location in a trailing-to-leading direction drives a seed from the seed discharge chamber through the hollow needle and into a prostate or other internal organ into which the needle is inserted.

The bias means is loop-shaped, its trailing end being longitudinally disposed in parallel relation to a longitudinal axis of symmetry of the applicator barrel and its leading end being disposed in radially-extending relation to said longitudinal axis. This loop shape, the plastic construction, and the empirically determined sizing and shaping of the loop member gives it the inherent resiliency required to urge each seed, sequentially, into the seed discharge chamber.

It is a primary object of this invention to provide an interstitial brachytherapy device that is much less expensive than the devices heretofore known.

A closely related object is to provide such a device that, due to its low expense, is disposable after use as ordinary waste and not as hazardous waste.

Another important object is to provide a device that enables its user to easily determine the number of seeds still within the cartridge of the device.

Still further objects are to provide a device that has an appearance with which physicians are familiar, that is small and light-in-weight, and which, due to its plastic construction, does not become radioactive with use.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
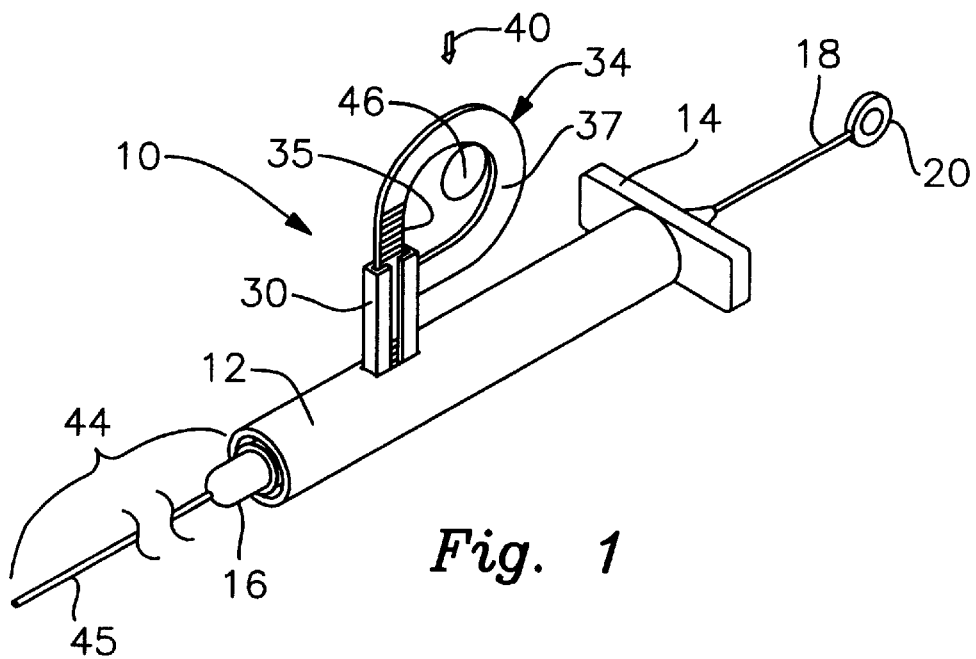
FIG. 1 is a perspective view of the novel applicator system when in its assembled configuration.

Referring now to FIG. 1, it will there be seen that an exemplary embodiment of the invention is denoted as a whole by the reference numeral 10.

Novel assembly 10 includes elongate barrel 12, flat handle 14 which is disposed transversely to the longitudinal axis of barrel 12 and secured to the trailing end thereof, and a nose member 16 that is positioned at the leading end thereof. These three elements of the invention present the general appearance of a hypodermic syringe; this facilitates use and acceptance of the novel device because, unlike the earlier applicators of this sort, how to hold and use the device is readily apparent. For reasons that will become clear hereinafter, barrel 12 is preferably formed of a transparent plastic.

The novel assembly further includes an elongate plunger rod 18 having a handle 20 at its trailing end. The leading end of plunger rod is denoted 22 on the left side of FIG. 1.

Figure 2:
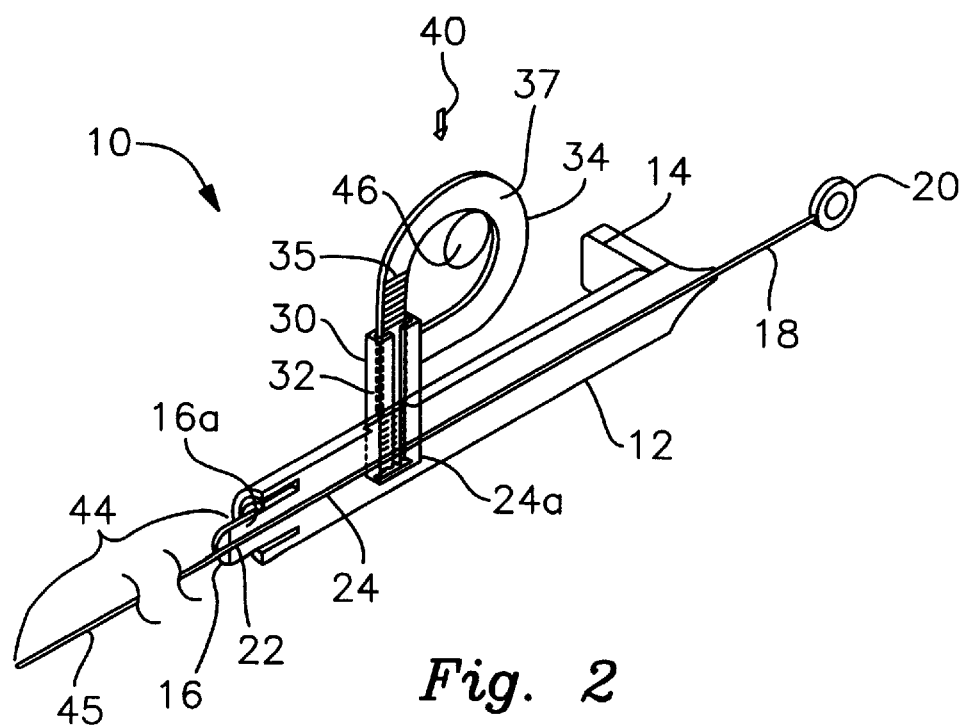
FIG. 2 is a partially cut-away perspective view of the parts when in their assembled configuration.

As best understood in connection with FIG. 2, plunger rod 18 is slidably received within an elongate throughbore 24 that is coextensive with the longitudinal axis of symmetry of barrel 12. Note that the longitudinal extent of plunger rod 18 is greater than the combined longitudinal extent of elongate throughbore 24 and needle 44. Handle 14 is centrally apertured to accommodate elongate plunger 18.

Figure 3:
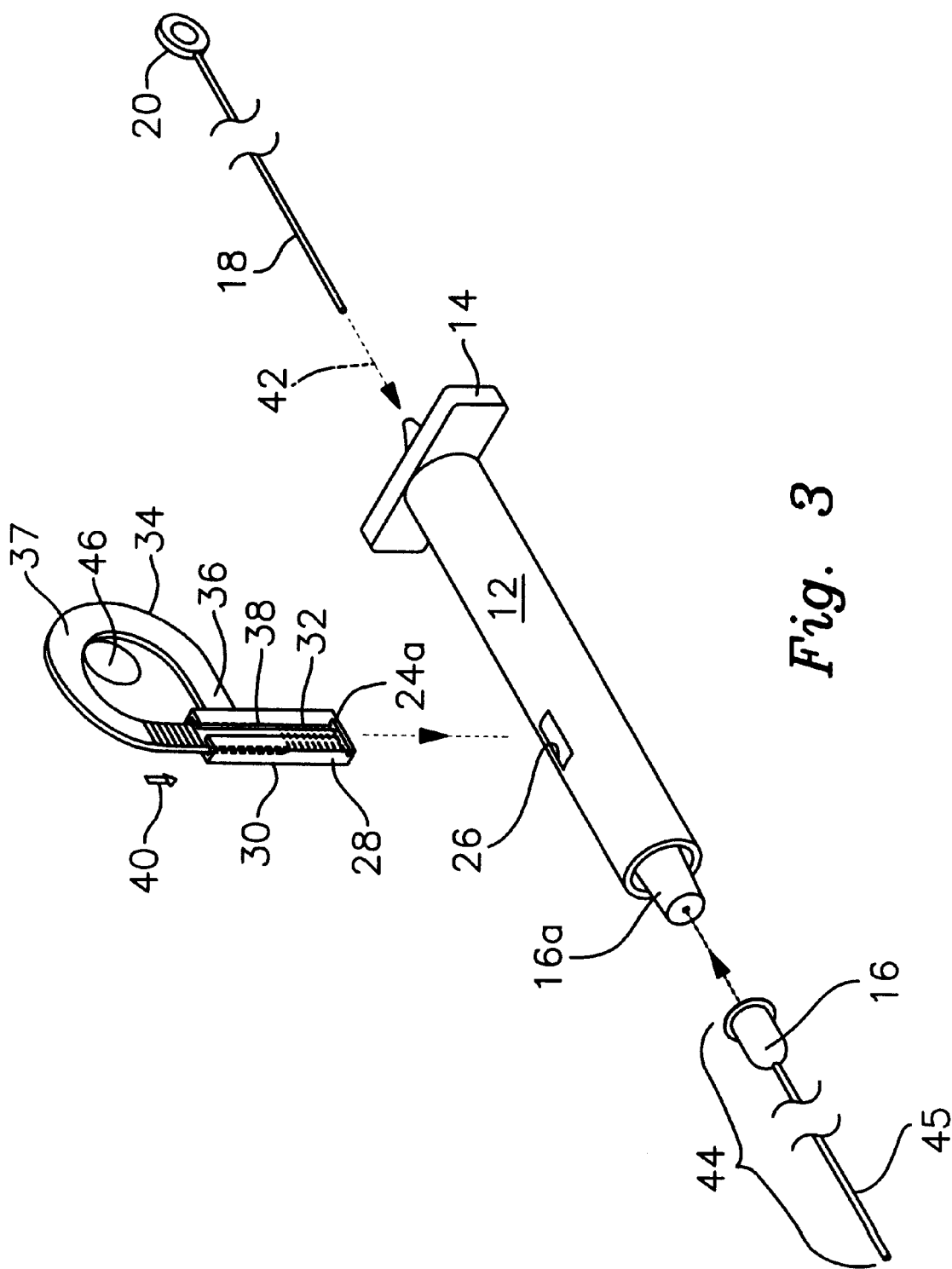
FIG. 3 is an exploded perspective view of the system of claim 1.

As best understood in connection with FIG. 3, a radially disposed opening 26 is also formed in barrel 12. Said opening 26 has a rectangular configuration so as to slidably receive the leading end 28 of novel cartridge 30. Cartridge 30 includes a hollow housing of parallelpiped form that may have any practical external configuration; opening 26 may be of any predetermined configuration that matches said external configuration of said hollow housing.

Note bore 24a formed in the radially innermost end of said hollow housing of cartridge 30; as perhaps best understood in connection with FIG. 2, bore 24a, hereinafter referred to as seed chamber 24a, aligns with throughbore 24 when cartridge 30 is fully seated within opening 26.

Cartridge 30 is formed of a transparent plastic, has a hollow construction and is specifically adapted and configured to slidably receive a plurality of horizontally disposed, vertically stacked seeds, collectively denoted 32. The vertical dimension of cartridge 30 substantially exceeds its width and depth dimensions, and said cartridge has an open top to slidably receive said seeds.

A bias means 34, preferably formed of a flexible and resilient plastic, has a trailing end 36 fixedly secured to or integrally formed with cartridge 30 and a leading end 38 that bears radially inwardly upon said stack of seeds 32, said direction being indicated by directional arrow 40. Trailing end 36 is longitudinally disposed in parallel relation to the longitudinal axis of barrel 12 and leading end 38 is disposed normal to said axis. Thus, middle section 37, formed integrally with said leading and trailing ends, is loop-shaped. The curvature and flexibility of the loop is predetermined so that the leading end of the plastic spring is positioned within the seed discharge chamber when said chamber is empty.

The bias provided by plastic spring 34 urges a single seed into seed chamber 24a and its force is sufficient to prevent said single seed from sliding out of chamber 24a under the force of gravity. The force, however, is insufficient to retain said single seed in place when plunger rod 18 is advanced in the direction of arrow 42; accordingly, advancing said plunger rod 18 in the direction of arrow 42, i.e., in a trailing-to-leading direction, displaces the single seed in seed chamber 24a into the prostate through throughbore 24 and through hollow needle 44 which is mounted to the leading end of barrel 12.

A plurality of graduation marks, collectively denoted 35, is formed on plastic spring 34 to provide an indication of the number of seeds remaining in the applicator at any time. More specifically, said plurality of graduation marks are imprinted upon the leading end of the plastic spring in vertically spaced apart relation to one another, the number of graduation marks being equal to the numerical seed-receiving capacity of the hollow housing. The graduation marks are spaced apart from one another by a distance substantially equal to the thickness of a seed so that the number of graduation marks on a part of the leading end of the plastic spring that is not received within the hollow housing is equal to the number of seeds remaining within the hollow housing. Thus, all of the graduation marks are external to the hollow housing when the hollow housing is filled to capacity with seeds and none of the graduation marks are external to the hollow housing when there are no seeds in the hollow housing.

The number of seeds can also be visually ascertained because cartridge 30 and barrel 12 are transparent.

Reference numeral 16a at the left end of FIG. 3 indicates the leading end of barrel 12. Needle 44 consists of the metal section (cannula) 45 and the nose or hub 16 of the needle. The needle hub 16 is releasably mounted to said leading end 16a. This construction enables the attachment of industry standard luer lock needles such as needle 44 to barrel 12, thereby obviating the need for special needles as in prior art constructions. More particularly, part 16a is an adaptor to which any luer lock needle may be mounted; elongate throughbore 24 extends through said adaptor.

The circular area denoted 46 represents an advertising label that performs an identification function.

Novel device 10, being formed of inexpensive plastic materials, may be disposed of after use. Since it is not cleaned or autoclaved, this eliminates the down time that is encountered in a treatment facility when a stainless steel, nondisposable applicator is used because cleaning and autoclaving are time-consuming procedures. Thus, surgical procedures may be scheduled at more frequent intervals when the novel applicator and cartridge are used.

Moreover, the plastic materials do not become radioactive with use and thus the novel structure can be disposed of as ordinary waste and not as a hazardous material.

The compact size and light weight of the novel structure also facilitates its use.

The method of use should be apparent. It includes the steps of inserting novel pre-loaded, self-biased cartridge 30 into opening 26 formed in barrel 12, attaching luer lock needle 44 to adapter 16a, inserting said needle into a prostate or other internal organ, and manipulating plunger rod 18 in the manner set forth above. Again, the use of a grid and the other surgical procedures employed in the art of interstitial brachytherapy need not be repeated here. How to hold and manipulate the novel device is self-evident, in contrast to the devices heretofore known.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:
1. An interstitial brachytherapy device, comprising:
an applicator;
a cartridge that is releasably connected to said applicator, said cartridge adapted to hold a plurality of radioactive seeds therewithin in vertically stacked relation to one another;
said applicator including an elongate barrel;
an elongate throughbore formed in said barrel coincident with a longitudinal axis of symmetry thereof;
a radially extending opening formed in said barrel having a radially innermost end in open communication with said elongate throughbore;
a seed discharge chamber formed in a radially innermost end of said cartridge, said seed discharge chamber aligning with said elongate throughbore when said cartridge is fully seated within said barrel;
a manually-operated, elongate plunger rod slidably mounted in said elongate throughbore;
a hollow needle detachably secured to said barrel at a leading end thereof;
a bias means, integrally formed with said cartridge, that automatically and continuously urges said seeds in said cartridge toward said seed discharge chamber, said seed discharge chamber being sized to receive only one seed at a time;
said bias means having a leading end that is positioned within said seed discharge chamber when said cartridge is empty;
whereby retraction of said plunger rod to a preselected location on a trailing side of said seed discharge chamber enables said bias means to automatically urge a seed into said seed discharge chamber when at least one seed is stored within said cartridge; and
whereby advancement of said plunger rod from said preselected location in a trailing-to-leading direction drives a seed from said seed discharge chamber through said needle and into an internal organ into which said needle is inserted.

2. The device of claim 1, wherein said bias means is an inherently biased plastic bias means.

3. The device of claim 2, wherein said bias means has a trailing end formed integrally with said cartridge, and wherein said leading end of said bias means is slidably received within a hollow interior of said cartridge.

4. The device of claim 3, wherein said bias means is loop-shaped, said trailing end being longitudinally disposed in parallel relation to said longitudinal axis of symmetry of said barrel and said leading end being disposed in radially-extending relation to said longitudinal axis.

5. The device of claim 1, wherein said applicator further comprises:
a needle-receiving adaptor being formed in said barrel at a leading end thereof so that preselected needles may be detachably secured to said adaptor;
said elongate plunger rod having a longitudinal extent greater than a combined longitudinal extent of said elongate throughbore and a needle secured to said adaptor.

6. The device of claim 5, wherein said barrel is made of plastic.

7. The device of claim 5, wherein said adaptor is a luer lock adaptor to enable use of industry standard hypodermic needles with said applicator.

8. The device of claim 5, further comprising a transversely disposed flat handle secured to said barrel at a trailing end thereof, said handle being centrally apertured to admit said plunger rod therethrough and said handle, together with said barrel, collectively providing a syringe-like appearance.

9. A cartridge that forms a part of an interstitial brachytherapy device, comprising:
a hollow housing having a generally parallelpiped construction;
said hollow housing having a vertical extent that substantially exceeds its respective width and depth extents;
said hollow housing having an open upper end adapted to slidingly receive a plurality of radioactive seeds that are vertically stacked with respect to one another;
a seed discharge chamber formed in a bottom of said housing;
said seed discharge chamber having a longitudinal axis disposed normal to a vertical axis of said hollow housing;
a bias means for urging seeds within said hollow housing toward said seed discharge chamber;
said bias means having a trailing end integrally formed with said hollow housing, said trailing end being disposed parallel to said longitudinal axis of said seed discharge chamber;
said bias means having a leading end slidably disposed within said hollow housing, said leading end being coincident with a vertical axis of symmetry of said hollow housing;
said bias means having a middle section of looped configuration formed integrally with said trailing and leading ends of said bias means.

10. The cartridge of claim 9, wherein said cartridge is made of plastic.

11. The cartridge of claim 9, wherein said cartridge is made of a clear plastic to facilitate viewing of seeds disposed therein.

12. The cartridge of claim 9, wherein said leading end of said bias means is disposed within said seed discharge chamber when no seeds are disposed within said hollow housing.

13. The cartridge of claim 12, further comprising a plurality of vertically spaced apart graduation marks imprinted upon said leading end of said bias means, the number of said graduation marks being equal to the numerical seed-receiving capacity of said hollow housing, said graduation marks being spaced apart from one another by a distance substantially equal to the thickness of a seed so that the number of graduation marks on a part of said leading end of said bias means that is not received within said hollow housing is equal to the number of seeds remaining within said hollow housing, all of said graduation marks being external to said hollow housing when said hollow housing is filled to capacity with said seeds and none of said graduation marks being external to said hollow housing when said hollow housing is empty.

14. A method for implanting radioactive seeds in a prostate or other internal organ, comprising the steps of:
providing a cartridge with a plurality of vertically stacked seeds, said cartridge including a seed discharge chamber in a preselected end of said cartridge and an inherently self-biased bias means, integral with said cartridge, for automatically and continuously urging said seeds toward said seed discharge chamber,
providing an elongate applicator having an elongate throughbore formed therein coincident with a longitudinal axis of symmetry of said applicator, said applicator including a radially-extending opening, said opening having a radially innermost end that is in open communication with said elongate throughbore, said opening configured to slidably receive said cartridge:
mounting a hollow needle at a leading end of said applicator;
inserting a plunger rod into said elongate throughbore from a trailing side of said seed discharge chamber, said plunger rod adapted for sliding in a trailing-to-leading direction to drive a seed in said discharge chamber out of said chamber, through said elongate throughbore, through the hollow interior of said hollow needle, and into an internal organ;
inserting the hollow needle into a patient at a treatment location in the internal organ: and
operating the plunger rod in the trailing-to-leading direction to drive a seed into the internal organ.

* * * * *